United States Patent
King

(10) Patent No.: US 10,008,298 B2
(45) Date of Patent: Jun. 26, 2018

(54) RADIATION-SHIELDING CURTAIN

(71) Applicant: Mettler-Toledo Safeline X-Ray Ltd., Hertfordshire (GB)

(72) Inventor: Nigel King, Bedfordshire (GB)

(73) Assignee: METTLER-TOLEDO SAFELINE X-RAY LTD., Hertfordshire (GB)

(*) Notice: Subject to any disclaimer, the term of this patent is extended or adjusted under 35 U.S.C. 154(b) by 0 days. days.

(21) Appl. No.: 15/289,422

(22) Filed: Oct. 10, 2016

(65) Prior Publication Data

US 2017/0032858 A1 Feb. 2, 2017

Related U.S. Application Data

(63) Continuation of application No. PCT/EP2015/057589, filed on Apr. 8, 2015.

(30) Foreign Application Priority Data

Apr. 10, 2014 (EP) .................................. 14164201

(51) Int. Cl.
| G21F 3/00 | (2006.01) |
|---|---|
| G21F 1/10 | (2006.01) |
| A61B 6/10 | (2006.01) |
| G21F 7/00 | (2006.01) |
| G21F 1/08 | (2006.01) |
| G01N 23/04 | (2018.01) |

(52) U.S. Cl.
CPC ................ G21F 3/00 (2013.01); A61B 6/107 (2013.01); G01N 23/04 (2013.01); G21F 1/08 (2013.01); G21F 1/10 (2013.01); G21F 7/00 (2013.01)

(58) Field of Classification Search
None
See application file for complete search history.

(56) References Cited

U.S. PATENT DOCUMENTS

| 2,759,534 | A | * | 8/1956 | Harju | E06B 9/367 |
| | | | | | 16/95 D |
| 3,967,129 | A | * | 6/1976 | Winkler | A61B 6/107 |
| | | | | | 160/332 |
| 4,020,346 | A | * | 4/1977 | Dennis | G01N 23/043 |
| | | | | | 250/519.1 |
| 4,062,518 | A | * | 12/1977 | Stivender | A61B 6/04 |
| | | | | | 250/519.1 |
| 4,877,964 | A | * | 10/1989 | Tanaka | A23L 3/28 |
| | | | | | 250/455.11 |
| 5,900,638 | A | * | 5/1999 | Jaeger | A61B 6/107 |
| | | | | | 250/515.1 |
| 2008/0149864 | A1 | * | 6/2008 | Hargrove | A61B 6/107 |
| | | | | | 250/515.1 |

(Continued)

FOREIGN PATENT DOCUMENTS

| CN | 201642070 U | 11/2010 |
| CN | 201879716 U | 6/2011 |

(Continued)

*Primary Examiner* — Michael Logie

(74) *Attorney, Agent, or Firm* — Standley Law Group LLP

(57) ABSTRACT

A radiation-shielding curtain (20) of the kind used at the conveyor entrance and exit openings of a radiographic inspection system or irradiation system is composed of a large number of straight, slender, vertically suspended rods (21) which have a convex outwardly rounded cross-sectional profile and a smooth low friction surface.

12 Claims, 5 Drawing Sheets

(56) References Cited

U.S. PATENT DOCUMENTS

| | | | |
|---|---|---|---|
| 2011/0058650 A1 | 3/2011 | Makino et al. | |
| 2013/0114788 A1* | 5/2013 | Crass | G21F 1/10 |
| | | | 378/57 |
| 2015/0272519 A1* | 10/2015 | Buchmeyer | A61B 6/107 |
| | | | 250/515.1 |

FOREIGN PATENT DOCUMENTS

| | | | |
|---|---|---|---|
| CN | 203217959 U | 9/2013 | |
| FR | 2119665 A5 * | 8/1972 | A47H 23/04 |
| GB | 431632 A * | 7/1935 | C03B 15/08 |
| JP | 4351901 B2 | 10/2009 | |
| JP | 4796333 B2 | 10/2011 | |
| JP | 3175410 U | 5/2012 | |
| JP | 2012-159355 A | 8/2012 | |
| JP | 2013-250170 A | 12/2013 | |

* cited by examiner

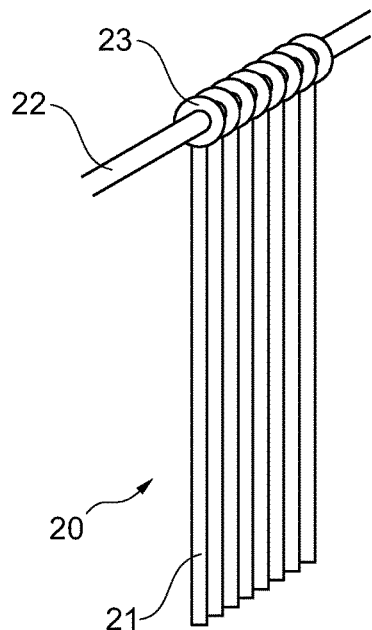
Fig. 2
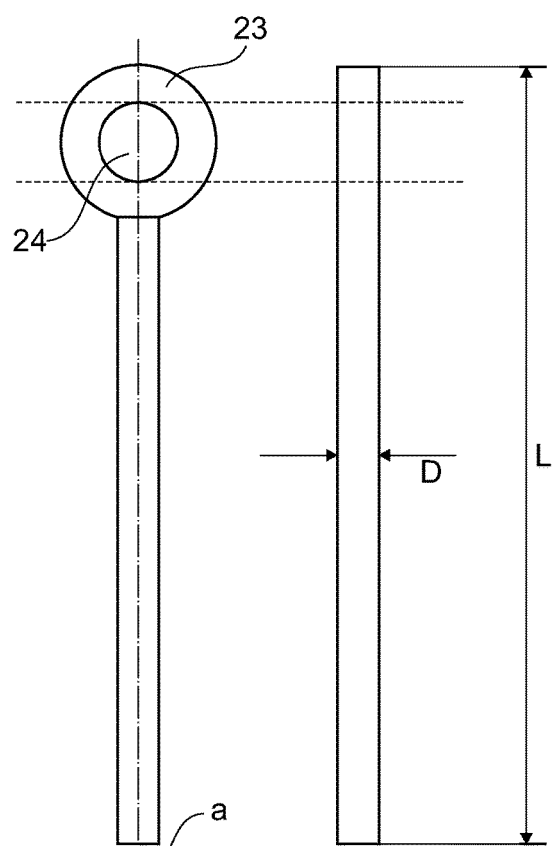
Fig. 3a
Fig. 3b
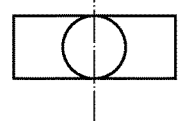
Fig. 3c

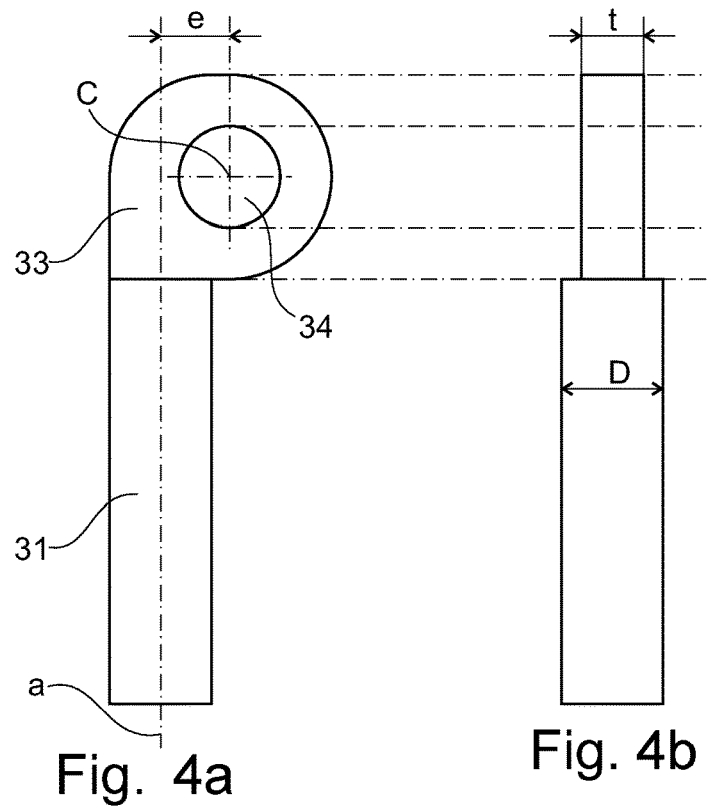
Fig. 4a  Fig. 4b
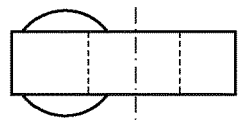
Fig. 4c
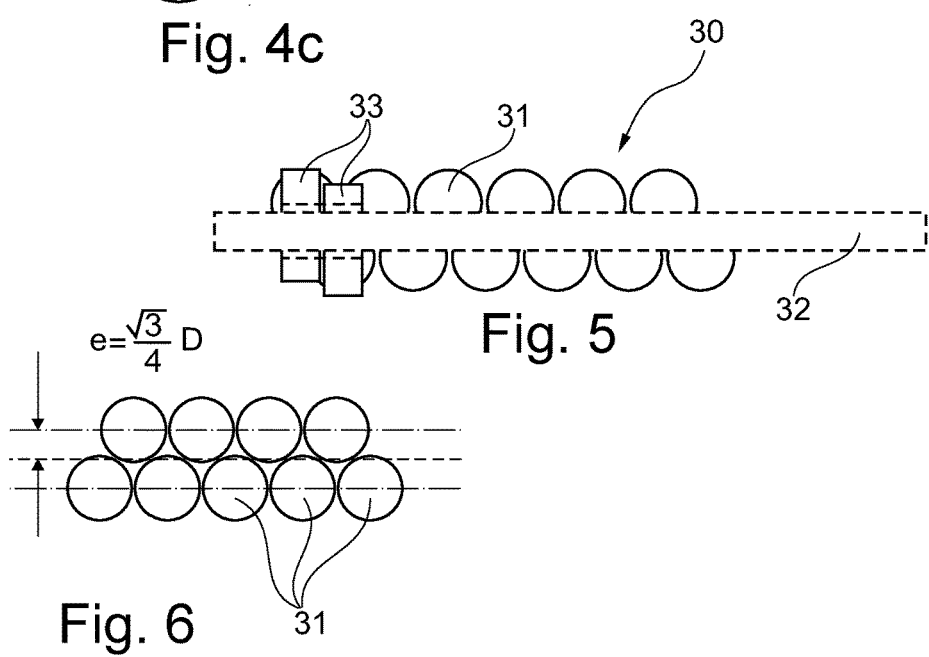
Fig. 5
Fig. 6

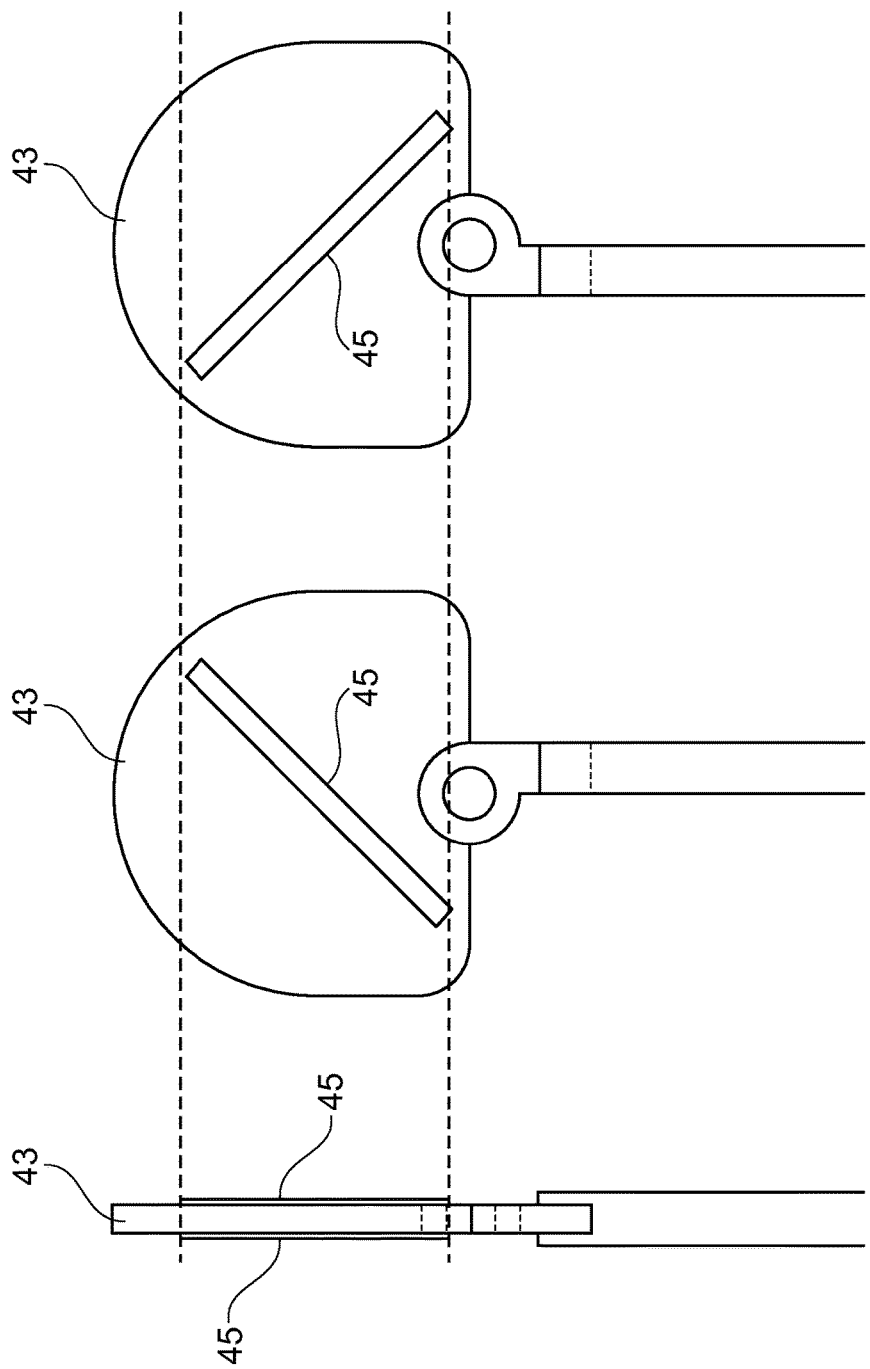

RADIATION-SHIELDING CURTAIN

CROSS-REFERENCE TO RELATED APPLICATIONS

This application is a bypass continuation of PCT/EP2015/057589, filed on 8 Apr. 2015, which in turn claims a right of priority under 35 USC § 119 from European patent application 14164201.7, filed on 10 Apr. 2014. The content of each application is incorporated by reference as if fully recited herein.

TECHNICAL FIELD

The invention relates to the field of in-line radiation equipment, i.e. systems where objects are exposed to radiation, for example for the purpose of inspection with transmitted or reflected radiation, or for germicidal irradiation.

BACKGROUND OF THE INVENTION AND RELATED PRIOR ART

X-ray scanner systems that are used to detect foreign objects and contaminants in food products and pharmaceutical products belong to the known state of the art. For safety reasons, the radiation in a scanner system or irradiation system of this type needs to be contained inside a cabinet-style enclosure with an entrance and an exit opening, and with a conveyor belt for transporting articles that are undergoing the inspection or irradiation through the entrance opening, through the inspection or irradiation area inside the enclosure, and out through the exit opening, as the articles pass through the inspection or irradiation system. In particular, the invention concerns the radiation-shielding curtains that are arranged at the entrance and exit openings of the cabinet-style enclosure of the system. A commonly familiar example of such an X-ray system with a conveyor belt and shielding curtains are the baggage inspection systems used at airports. The invention further includes radiographic inspection systems and irradiation systems equipped with at least one shielding curtain according to the invention.

In their most common form, the shielding curtains are vertically slit sheets of rubber or of a rubber-like material containing a radiation-blocking component such as lead oxide or tungsten, for example as a sandwiched laminate or in distributed form. An entire entrance- or exit curtain can consist of a single sheet, but typically two or three sheets are arranged one after another at both the entrance and the exit opening of the inspection cabinet. Most curtains are configured as a close coupled pair on one hanger with the slits of one curtain offset against the slits of the other, so as to minimize the leakage, as the individual strips can sometimes twist and be distorted.

With the large numbers of objects passing through an inspection system, the impact and friction between the objects and the curtain will cause wear and tear on the latter. In addition, if the objects being inspected are for example unpackaged meats, poultry or fish, the curtains (as well as all other exposed parts of the system) will be subjected to rigorous cleaning and sanitizing, typically with steam or hot water. As a result, the curtain may become brittle, and the unpackaged food products could become contaminated by fragments of the crumbling curtain material.

A state-of-the-art X-ray inspection system with radiation-shielding curtains in the form of slit flexible sheets is described and illustrated in EP 2 194 373 A1. To alleviate the problem of mechanical wear and tear, an X-ray shielding curtain with a tungsten-containing layer is proposed which includes one or more protective layers of a polyolefin resin laminated on the tungsten-containing layer. Test results are presented to demonstrate improved resistance to peeling and chipping with 6 and 9 million passages of test objects. However, the aspect of cleanability, i.e. resistance to aggressive high-temperature cleaning processes, is not addressed in this reference.

Another example of an X-ray inspection system with radiation-shielding curtains in the form of slit flexible sheets is described and illustrated in JP 4351901 B2. A modular curtain unit with three slit curtain sheets, a suspension frame and a quick-release mounting arrangement is proposed to facilitate cleaning, maintenance and replacement of the curtains. Like the first example, this system with its slit rubber curtains does not appear to be suitable for applications that involve the heavy-duty cleaning and sanitizing which is required in the food industry.

In an X-ray inspection system described in JP 4796333 B2, the objective is to reduce mechanical wear and tear on the radiation-shielding curtains, specifically due to impact and friction at hard corners and edges of block-shaped objects such as products in boxes. The objects have to be of identical size and shape and lined up in a defined travel path on the conveyor belt. The curtain has hard, metallic sections meeting the corners and edges of the objects, and soft flexible sections meeting the front of the object or hanging outside the hard, metallic sections. The system can be set up for different-sized objects by adjusting the positions of the hard, metallic sections. Like the first example above, this system only aims to reduce mechanical wear and tear, but does not address the problems of cleaning and sanitizing the curtains with hot water and steam.

The foregoing examples illustrate a drawback which, in the experience of the applicant, is common to all shielding curtains made of rubber or any other flexible materials, i.e. their inability to meet the requirements of the food industry, particularly in applications where the shielding curtain comes into contact with unpackaged food products.

A radiation-shielding curtain described in JP 2012159355 A is divided into narrow vertical elements that are suspended from a curtain rod, analogous to the strips of the slit sheet curtains described above, but with the difference that the elements are stainless steel sheet metal stampings with a channel profile over part of their lengths for stiffness. The bottom ends of the curtain strips are curved in the downstream direction of the inspection path to make them glide more easily over the moving inspection objects. A stop device prevents swing-back of the curtain elements in the upstream direction and also keeps the curtain elements in a slightly inclined position which further eases the sliding contact between the inspection objects and the curtain elements.

A further X-ray inspection system which is described in JP 03175410 U has a radiation-shielding curtain divided into vertical elements like in all of the previous examples, but is specifically adapted to unpackaged food items which are transported through the inspection system in an open rectangular bin or other box-like container whose walls are higher than the top of the contents. The curtain elements overlap each other in such a way that when a bin travels through the curtain, any element pushed up by the moving bin will also lift up the next element on the side towards the center of the transport path. Thus, as long as the outermost elements are pushed up by the sidewalls of the moving bin, they will also hold up all of the elements lying between them, so that all elements in the path of the bin are lifted together as one flat sheet and no curtain element comes into contact with the contents of the open bin. Stainless steel and tungsten are mentioned as possible materials for the curtain elements, as well as the possibility of attaching a counterweight to each element above its point of suspension, which would allow the curtain to be pushed up more easily by the moving bin.

Of the five examples of state-of-the-art shielding curtains cited above, the first three, EP 2 194 373 A1, JP 4351901 B2 and JP 4796333 B2, are made at least in part of rubber or a rubber-like material which makes them unsuitable for applications where they would come into contact with unpackaged food, in particular meat, poultry and seafood, and would be subject to daily cleaning with hot water or steam.

In the fourth example, JP 2012159355 A, the curtain is made of stainless steel and at least in principle meets the requirement of cleanability, although there could be some concern about contaminants accumulating along the inside edges of the channeled profiles of the curtain elements. Furthermore, the sheet-metal curtain elements may not drape themselves closely against the objects moving through the curtain and there could be some scraping and jamming between the exposed lateral edges of the sheet-metal stampings and the objects moving through the curtain.

The radiation-shielding curtain of the fifth example, JP 03175410 U, if made of stainless steel and/or tungsten, could likewise meet the requirement of cleanability. On the other hand, this curtain with its overlapping elements is designed for the specific, limited application described above, which could actually prevent the curtain elements from gliding closely over the surface of irregular-shaped inspection objects. Also, if the curtain elements are made in the form of sheet-metal stampings, there would be the same concern about scraping and jamming between the exposed lateral edges of the curtain elements and the objects moving through the curtain.

OBJECT OF THE INVENTION

In view of the drawbacks and concerns with the state-of-the-art radiation-shielding curtains described above, it is therefore the object of the present invention to propose a radiation-shielding curtain for use in a radiographic inspection system or in an irradiation system, which is made of materials that can withstand the harsh cleaning methods required by sanitary standards in the food-processing and pharmaceutical industries, which is of a configuration that facilitates cleaning and allows the curtain to glide easily over the objects moving through the system and to drape itself closely against the surface of the moving objects, so as to provide an effective radiation shield at the entrance and/or exit openings of the inspection system.

SUMMARY OF THE INVENTION

The foregoing objectives are met by a radiation-shielding curtain and by an X-ray inspection system or an X-ray irradiation system, according to the appended claims. Further developed embodiments and features of the radiation-shielding curtain according to the invention are also presented.

A radiation-shielding curtain according to the invention is designed for use in an X-ray inspection system or in an X-ray irradiation system—for example a system providing ionizing radiation for product irradiation purposes in sterilization applications—with a cabinet-style enclosure serving to contain the radiation and having an entrance and an exit opening, and with a conveyor belt for transporting objects that are to be inspected or irradiated through the entrance opening, through the inspection or irradiation area inside the enclosure, and out through the exit opening, wherein radiation-shielding curtains are arranged at the entrance opening and/or at the exit opening of the cabinet-style enclosure of the X-ray inspection or X-ray irradiation system, and wherein the radiation-shielding curtain comprises elongate vertical elements suspended at the top and configured to be pushed out of the way by the objects moving through the curtain.

In particular according to the invention, each of the elongate elements of the radiation shielding curtain is a slender rod with a convex outwardly rounded cross-sectional profile and a smooth, low friction surface. This includes for example round, elliptic, oval and round-cornered polygonal shapes. Preferably, the low friction surface is a polished surface.

In preferred embodiments of the invention, the slender rods that constitute the curtain elements have a solid circular cross-sectional profile, in other words, the curtain elements are configured as solid cylindrical rods.

Alternatively, the slender rods that constitute the curtain elements could have a hollow circular cross-sectional profile, in other words, they could be configured as slender tubes. However, the ends of the tubes would have to be hermetically sealed in order to prevent any materials from entering into the tubes.

Advantageously, the slender rods that constitute the curtain elements are smoothly rounded at their lower ends, so that the ends will glide easily over the objects moving through the curtain and will not cause damage to the objects.

In accordance with the stated objective of the invention, the curtain elements or at least all of their exposed surfaces should be of a material that meets the sanitary requirements of the food industry.

Preferably, the curtain elements or at least all of their exposed surfaces are of a corrosion- and abrasion-resistant metal such as stainless steel and/or tungsten or, in general terms, a material suitable to be in direct contact with foodstuffs.

Alternatively, it is conceivable to make the curtain elements of a polymer material that meets the sanitary requirements of the food industry, with a radiation-absorbing component either layered on the surface of the rod or imbedded in the rod as a distributed filler material.

The inventive configuration of the shielding curtain with its multitude of slender rods is very advantageous in that it meets all of the objectives stated above. The slender rods with their smooth, round or at least convex surfaces will glide easily over the objects moving through the curtain, and the entire curtain of thin, densely hung, contiguously adjacent rods will drape itself tightly over the moving object. In other words, one of the main advantages of the invention is the high resolution with which the smooth and slender rods adapt themselves to the flanks of the object moving through the curtain. If the curtain elements were, for example, 12 mm wide stainless steel sheet metal strips (analogous to the rubber strips in inspection systems), an entire element would open even if only 1 mm of the object flank were in contact with it. As the rods are made of a corrosion- and abrasion-resistant metal such as stainless steel and/or tungsten, they will easily withstand the impact and friction of the moving objects as well as any harsh cleaning methods that they may be exposed to.

It goes without saying that the field of application for this radiation-shielding curtain is not limited to the food-processing industry. For new or existing radiographic inspection systems or irradiation systems, the invention may offer an advantageous alternative to the radiation-shielding curtains of the prior art described hereinabove.

In accordance with the invention, the rods that make up the radiation-shielding curtain can be suspended side-by-side from a horizontal rail. Two or more rows of rods, each row suspended from its own horizontal rail, could be arranged both at the entrance opening and at the exit opening.

To suspend the rods from the horizontal rail, each of the rods preferably has at its upper end, relative to the suspended position, a hanger portion with an eyelet which, in the assembled state of the shielding curtain, is traversed by the horizontal rail.

In a particularly preferred embodiment of the invention, the hanger portion is flattened to a thickness of less than the rod diameter D, the eyelet is laterally offset from the centerline of the rod by an amount in the order of D/2, and the rods are hung from the horizontal rail with the laterally offset eyelets in alternatingly reversed positions. With this arrangement, two rows of rods, i.e. a double-layered curtain, can be suspended from one horizontal rail with the rods of one layer offset against the rods of the other layer, whereby the shielding capability of the curtain is vastly enhanced.

According to a particularly preferred design choice in the foregoing embodiment, the hanger portion is flattened to a thickness corresponding to essentially half the rod diameter D, the eyelet is laterally offset from the centerline of the rod by a distance equaling at least $$\frac{\sqrt{3}}{4}D,$$

and the rods are hung from the horizontal rail with the laterally offset eyelets in alternatingly reversed positions.

With the latter arrangement, the rods can be suspended from the horizontal rail in a so-called "tightest-packing" mode where each rod, except those at the ends of the curtain, is in direct contact with four neighboring rods.

In a further preferred embodiment, the hanger portion is expanded into a plate with dimensions parallel to the plate surface an order of magnitude larger, for example at least five times larger, than the rod diameter D.

These plate-shaped hanger portions have the advantage that their tight lineup on the horizontal rail essentially constrains the suspended rods to move in a plane that is perpendicular to the horizontal suspension rail and essentially prevents the rods from being pushed sideways by the objects moving through the curtain.

The center of gravity of the plate-shaped hanger portion can be offset from the centerline of the rod in the same direction as the eyelet and by a larger distance than the latter, so that the combined center of gravity of the rod including the hanger portion lies vertically below the center of the eyelet and the rod will hang from the horizontal rail in a substantially vertical rest position.

In addition, the center of gravity of the plate-shaped hanger portion can be located higher than the eyelet, so as to reduce the restoring moment of the physical pendulum formed by the curtain element including the hanger portion. Thus, the rods can be moved more easily by the objects traveling through the curtain on a conveyor belt.

A radiographic inspection system or an irradiation system according to the invention includes a cabinet-style enclosure that serves to contain the radiation and has an entrance and an exit opening, and a conveyor belt for transporting objects that are to be inspected or irradiated through the entrance opening, through the inspection or irradiation area inside the enclosure, and out through the exit opening. In particular, the radiographic inspection system or irradiation system is distinguished by having at least one radiation-shielding curtain of the foregoing description arranged at the entrance opening and/or at the exit opening of the cabinet-style enclosure.

BRIEF DESCRIPTION OF DRAWINGS

The following description of specific embodiments and details of the invention is supported by the attached schematic drawings, wherein:

FIG. 2 shows a radiation-shielding curtain according to a first embodiment of the invention;

FIGS. 3a, 3b and 3c show the hanger portion of one element of the radiation-shielding curtain of FIG. 2 in three projections;

FIGS. 4a, 4b and 4c show the hanger portion of one element of a radiation-shielding curtain according to a second embodiment of the invention in three projections;

FIG. 5 is a top plan view of a two-layered curtain with curtain elements according to FIGS. 4a to 4c;

FIG. 6 schematically illustrates a densest-packing arrangement of the curtain elements;

FIGS. 9a, 9b and 9c show a variation of the curtain element of FIGS. 5 and 6.

DETAILED DESCRIPTION OF SPECIFIC EMBODIMENTS OF THE INVENTION

Figure 1:
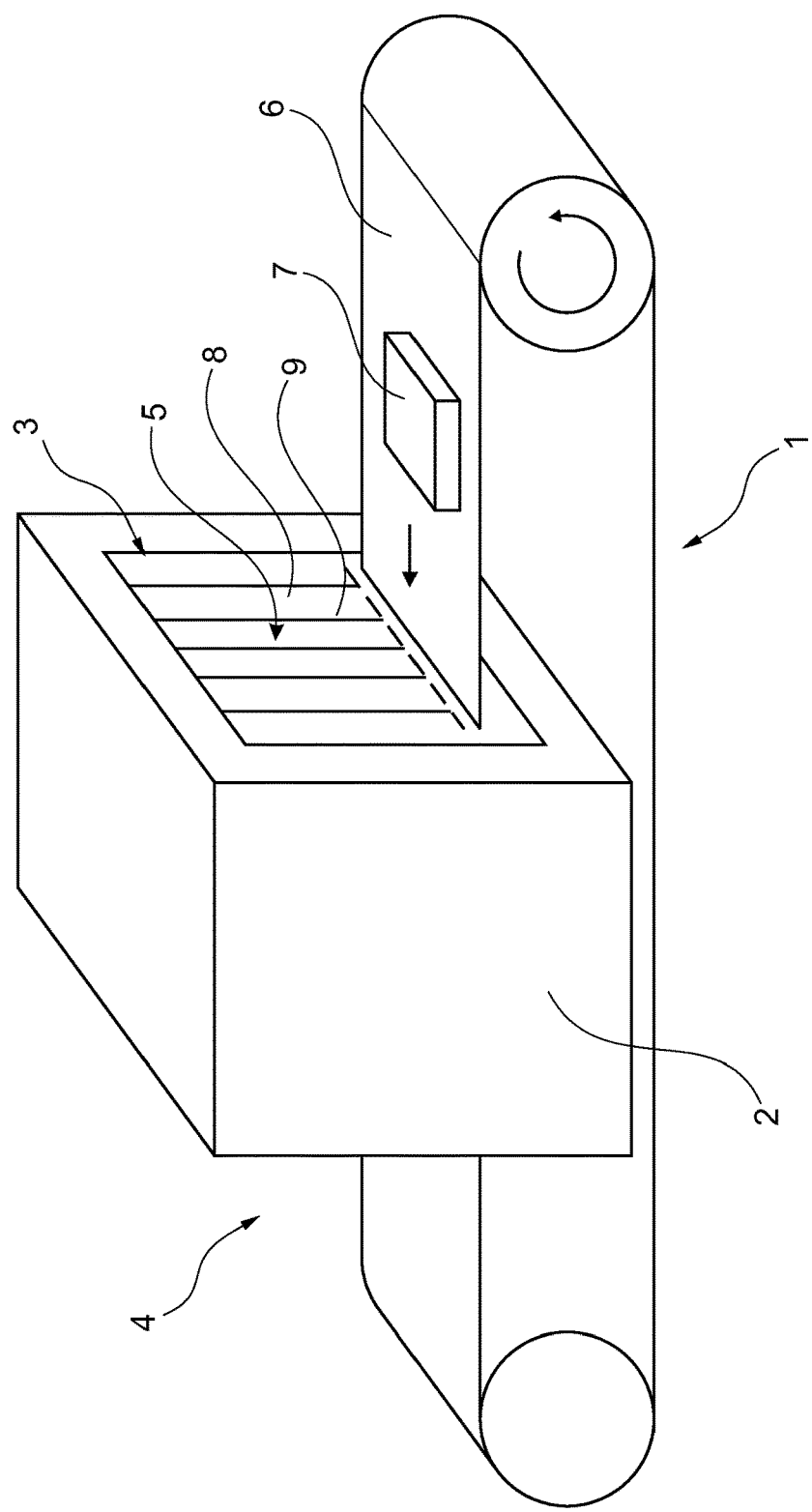
FIG. 1 illustrates a radiographic inspection system with a radiation-shielding curtain at the conveyor entrance.

FIG. 1 schematically illustrates a radiographic inspection system 1, specifically an X-ray scanner system of the kind used, for example, in the food- and pharmaceutical industries to detect foreign objects and contaminants in products. An inspection system or scanner system 1 of this type has a stationary radiation source (not visible in the drawing) and a stationary linear detector array (not visible in the drawing) arranged inside a cabinet-style enclosure 2 with an entrance opening 3 and an exit opening 4 (not visible). As can be seen in this drawing, the entrance opening 3 is closed off by a radiation-shielding curtain 5. Normally, the exit opening 4 is closed off likewise by another radiation shielding curtain 5 of the same kind. The inspection system 1 further includes a conveyor belt 6 for transporting articles 7 under inspection through the entrance opening 3, through a space between the radiation source and the detector array inside the enclosure 2, and out through the exit opening 4, as the articles 7 pass through the inspection system 1.

The shielding curtains 5 in their most common form are sheets of rubber or of a rubber-like material divided into vertical strips 8 by slits 9 and containing a radiation-blocking component such as lead oxide or tungsten, for example as a sandwiched laminate or in distributed form. Typically, a shielding curtain 5 can be configured as a close coupled pair of such slit sheets arranged on one hanger with the vertical strips 8 of one sheet covering the slits 9 of the other sheet, so as to minimize the leakage of radiation to the outside.

As mentioned previously herein, if the objects or articles 7 being inspected are for example unpackaged meats, poultry or fish, the curtains 5 (as well as all other exposed parts of the system) will be subjected to rigorous cleaning and sanitizing, typically with steam or hot water. As a result, the curtain may become brittle, and the unpackaged food products could become contaminated by fragments of the crumbling curtain material. Inspection systems 1, and in particular radiation-shielding curtains 5 used in such applications are therefore subject to stringent regulatory requirements and approvals.

FIG. 2 shows a radiation-shielding curtain 20 which embodies the inventive concept of a radiation-shielding curtain composed of slender rods 21 suspended adjacent to each other from a horizontal rail 22. To suspend the rods 21 from the horizontal rail 22, each of the rods 21 has at its upper end, relative to the suspended position, a hanger portion 23 with an eyelet 24 which, in the assembled state of the shielding curtain 20, is traversed by the horizontal rail 22. The individual rod 21 has a compact, externally convex cross-sectional profile and a smooth surface. In particular, the rods 21 of the illustrated curtain 20 have a round, i.e. circular profile, but other convex and outwardly rounded profiles are also possible. The attribute "slender" in this context means that the diameter D of the rod is small in comparison to its length. Only as an example, the rod 21 could have a diameter of D=5 mm and a length L of 200 mm.

As mentioned earlier, the term "rod" in this context can refer to a rod with a solid cross-section or also to a rod of a hollow, tubular cross-section. In the latter case the ends of the tubes would have to be hermetically sealed in order to meet sanitary requirements in food industry.

Further details of the hanger portion 23 of an element or rod 21 of the radiation-shielding curtain 20 are shown in FIGS. 3a, 3b and 3c. FIG. 3a shows the hanger element in a side elevation view, that is, in the direction of the horizontal rail 22. FIG. 3b shows the same element in a front elevation view, that is, in a horizontal direction perpendicular to the rail 22 and FIG. 3c shows the hanger element viewed in plan view from below. In this embodiment of the radiation-shielding curtain the eyelet 24 of the hanger portion 23 is centered on the axis a of the rod 21.

To minimize the amount of radiation escaping through the gaps between the rods 21 of the shielding curtain 20 of FIGS. 2 and 3a to 3c, one could, of course, arrange two or more shielding curtains 20 one after another and close together both at the entrance opening and at the exit opening. However, a preferred solution to minimize the amount of radiation escaping through the gaps between the rods of the shielding curtain is illustrated in FIGS. 4a through 4c and FIG. 5.

FIGS. 4a through 4c show the hanger portion 33 of an element or rod 31 of a radiation-shielding curtain 30 in three projections, that is, in side elevation view in the direction of the horizontal rail 32 (FIG. 4a), in a front elevation view in a horizontal direction perpendicular to the rail (FIG. 4b) and in a top plan view in the vertical direction (FIG. 4c). In this second embodiment of a radiation-shielding curtain 30, the hanger portion 33 is flattened to a thickness t of less than the rod diameter D, and the eyelet 34 is laterally offset from the axis a of the rod by an amount e in the order of D/2 (for clarity's sake, FIG. 4 shows an offset e somewhat larger than D/2).

FIG. 5 schematically represents the arrangement of a curtain 30 in which the rods 31 with the laterally offset hanger eyelets 34 shown in FIGS. 4a to 4c are hung from the horizontal rail 32 in positions alternatingly rotated by 180° about the centerline axes of the rods 34 and with the flattened hanger portions 33 substantially abutting each other. Thus, two rows of rods 34, i.e. a double-layered curtain 30, can be suspended from one horizontal rail 32 with the rods 31 of one layer offset against the rods 31 of the other layer, whereby the shielding capability of the curtain 30 is vastly enhanced.

FIG. 6 illustrates a particularly preferred design choice for the embodiment of FIGS. 4a to 4c, wherein the hanger portion 33 is flattened to a thickness t=D/2 and the eyelet is laterally offset from the centerline of the rod by a distance $$e = \frac{\sqrt{3}}{4}D.$$

This results in a so-called "densest-packing" arrangement in which each of the rods 31 (except the rods at the end of the curtain) directly touches four neighboring rods 31.

Figure 8:
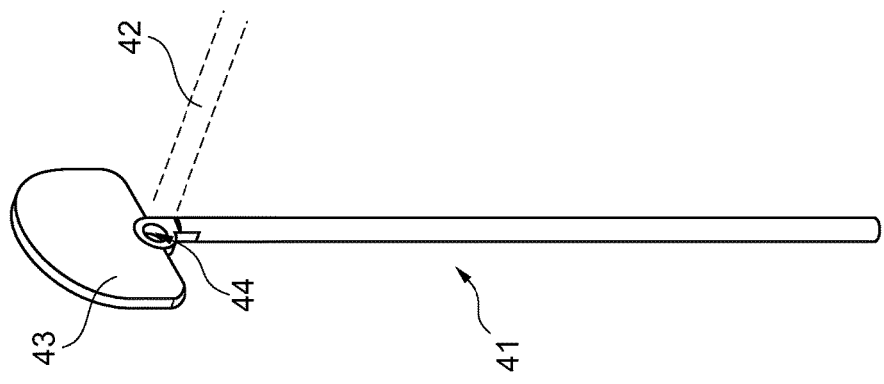
FIG. 8 shows the curtain element of FIGS. 7a and 7b in a perspective view.
Figure 7B:
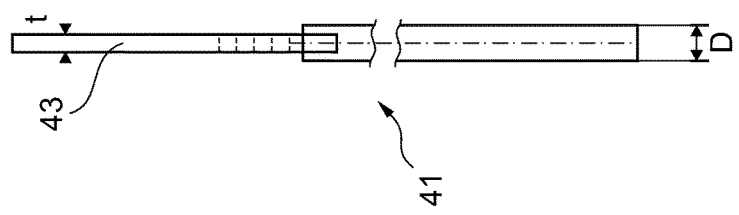
FIGS. 7a and 7b show the hanger portion of one element of a radiation-shielding curtain according to a third embodiment of the invention in two projections.
Figure 7A:
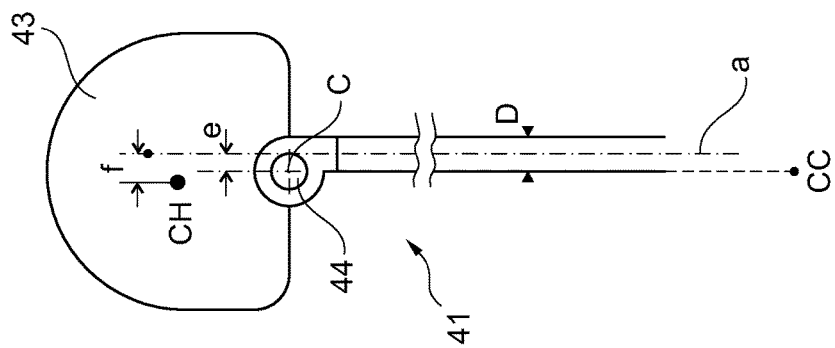

In a further preferred embodiment which is shown in FIGS. 7a, 7b and FIG. 8, the hanger portion 43 is expanded into a plate with dimensions parallel to the plate surface an order of magnitude larger than the rod diameter D. FIG. 7a is a side elevation view and FIG. 7b is a front elevation view. FIG. 8 is a perspective view.

These plate-shaped hanger portions 43 have the advantage that their tight lineup on the horizontal rail essentially constrains the suspended rods 41 to move in a plane that is perpendicular to the horizontal suspension rail and essentially prevents the rods 41 from being pushed sideways by the objects moving through the curtain.

The center of gravity CH of the plate-shaped hanger portion 43 can be offset from the centerline of the rod in the same direction as the eyelet 44 and by a larger amount f than the offset e of the eyelet 44, so that the combined center of gravity CC of the rod 41 including the hanger portion 43 lies vertically below the center C of the eyelet and the rod 41 will hang from the horizontal rail 42 in a substantially vertical rest position. Furthermore, the center of gravity CH of the plate-shaped hanger portion 43 is preferably located higher than the eyelet 44, so as to reduce the restoring moment of the physical pendulum formed by the rod 42 including the hanger portion 43. Thus, the rods can be moved more easily and the entire curtain offers less resistance to the objects traveling on a conveyor belt.

FIGS. 9a through 9c show a variation of the curtain element of FIGS. 7a, 7b and 8. Raised ridges 45 running in an approximately diagonal direction are arranged on both sides of the plate-shaped hanger portion 43. In FIG. 9a, a front elevation view is in the plane of the hanger portion 43 and FIGS. 9b and 9c are side elevation views normal to the plane of the hanger portion 43. FIGS. 9b and 9c show two curtain elements that are rotated by 180° relative to each other. Thus, as the elements in the assembled curtain are arranged in alternatingly flipped positions, the ridges of neighboring curtain elements will cross each other and have contact with each other only at the crossing point. The purpose of this feature is to reduce friction between the plate-shaped hanger portions of neighboring curtain elements, allowing the individual rods of the curtain to swing more freely.

Although the invention has been described through the presentation of specific examples of embodiments, it will be evident to the reader that numerous further variant embodiments could be developed from the teachings of the present invention, for example by varying the shapes and dimensions of any of the features and elements of the radiation-shielding curtain, or by combining the features of the individual examples with each other and/or by interchanging individual functional units between the embodiments described herein. It goes without saying that any such variant embodiments are considered to be part of the present invention. Likewise, while in detail having been described for an radiographic inspection system the inventive concept is applicable to other in-line radiation equipment, for example for the purpose of germicidal irradiation.

What is claimed is:

1. A system for inspecting or irradiating objects with radiation, the system comprising:
   a cabinet-style radiation-containment enclosure having an entrance opening and an exit opening with an inspection or irradiation area inside between the openings;
   a conveyor belt for transporting the objects into, through and out of the radiation-containment enclosure; and
   located at the entrance opening, the exit opening, or both, a radiation-shielding curtain, the curtain comprising:
      a plurality of elongate elements, each elongate element comprising a hanger portion at a top end of the elongate element with an eyelet located in the hanger portion and a straight rod with a convex outwardly rounded cross-sectional profile and a smooth low friction surface, and
      a horizontal rail that traverses the respective eyelets of the elongate elements such that the elongate elements are suspended vertically side-by-side therefrom, with the elongate elements arranged adjacent to each other for independent movement when pushed by the objects moving through the curtain with adjacent rods are hung from the horizontal rail rotated by 180° about the centerline axis of the rod, with the hanger portions in substantially abutting relationship;
      wherein each hanger portion has a flattened thickness of less than a diameter of the rod and the eyelet is offset laterally from a longitudinal centerline axis of the rod by approximately one-half of the rod diameter.

2. The system of claim 1, wherein each of the rods is configured as a solid cylindrical rod.

3. The system of claim 1, wherein each of the rods is configured as hollow cylindrical tubes having hermetically sealed ends.

4. The system of claim 1, wherein each of the rods is configured with a smoothly rounded lower end.

5. The system of claim 1, wherein at least all of the exposed surfaces of each rod are of a corrosion- and abrasion-resistant metal selected from the group consisting of stainless steel, tungsten and mixtures thereof.

6. The system of claim 1, wherein each of the rods, or at least a core portion thereof, comprises an injection-molded polymer material.

7. The system of claim 1, wherein the hanger portion is configured as a plate with dimensions parallel to the plate surface at least five times larger than the rod diameter.

8. The system of claim 7, further comprising:
   a raised ridge on each of the flat surfaces of the hanger portion, the raised ridge running in a direction approximately diagonal to the rod centerline.

9. The system of claim 8, wherein:
   each hanger portion has a center of gravity that is offset from the rod centerline in the same direction as the eyelet, the center of gravity being offset by a larger distance than the center of the eyelet, such that the elongate element has a combined center of gravity that lies vertically below the center of the eyelet, and the elongate element hangs in a substantially vertical rest position from the horizontal rail.

10. The system of claim 8, wherein:
    each hanger portion has a center of gravity that is located vertically above the eyelet, thereby reducing a restoring moment of a pendulum formed by the elongate element.

11. The system of claim 7, wherein:
    each hanger portion has a center of gravity that is offset from the rod centerline in the same direction as the eyelet, the center of gravity being offset by a larger distance than the center of the eyelet, such that the elongate element has a combined center of gravity that lies vertically below the center of the eyelet, and the elongate element hangs in a substantially vertical rest position from the horizontal rail.

12. The system of claim 7, wherein:
    each hanger portion has a center of gravity that is located vertically above the eyelet, thereby reducing a restoring moment of a pendulum formed by the elongate element.

* * * * *